United States Patent
Baldus

(10) Patent No.: US 10,065,159 B2
(45) Date of Patent: Sep. 4, 2018

(54) NITROUS OXIDE GAS MIXER FOR GENERATING A NITROUS OXIDE GAS MIX

(71) Applicant: BALDUS MEDIZINTECHNIK GMBH, Urbar (DE)

(72) Inventor: Fabian Baldus, Vallendar (DE)

(73) Assignee: BALDUS MEDIZINTECHNIK GMBH (DE)

( * ) Notice: Subject to any disclaimer, the term of this patent is extended or adjusted under 35 U.S.C. 154(b) by 231 days.

(21) Appl. No.: 15/099,415

(22) Filed: Apr. 14, 2016

(65) Prior Publication Data

US 2016/0310918 A1 Oct. 27, 2016

(30) Foreign Application Priority Data

Apr. 27, 2015 (EP) ..................................... 15001240
Feb. 23, 2016 (EP) ..................................... 16000433

(51) Int. Cl.
*B01F 13/04* (2006.01)
*B01F 15/02* (2006.01)
(Continued)

(52) U.S. Cl.
CPC ............ *B01F 13/045* (2013.01); *A61K 33/00* (2013.01); *A61M 16/104* (2013.01); *A61M 16/1015* (2014.02); *A61M 16/12* (2013.01); *A61M 16/20* (2013.01); *B01F 13/04* (2013.01); *B01F 15/0022* (2013.01); *B01F 15/00149* (2013.01);
(Continued)

(58) Field of Classification Search
CPC ............ A61M 16/1015; A61M 16/104; A61M 16/12; A61M 16/20; A61M 16/208; A61M 2016/0027; A61M 2016/003; A61K 33/00; B01F 15/00148; B01F 15/00162; B01F 15/00175; B01F 15/0022; B01F 15/00305; B01F 15/00311; B01F 15/00402;
(Continued)

(56) References Cited

U.S. PATENT DOCUMENTS

| | | | |
|---|---|---|---|
| 2,406,129 A | 8/1946 | Blease | 73/198 |
| 4,034,753 A | 7/1977 | Connel | 128/188 |

(Continued)

FOREIGN PATENT DOCUMENTS

| | | | |
|---|---|---|---|
| CN | 203777444 | 8/2014 | A61M 16/01 |
| DE | 2643927 | 4/1977 | A61M 16/01 |

(Continued)

OTHER PUBLICATIONS

European Search Report issued in application No. 15001240.9, dated Oct. 14, 2015 (11 pgs).
(Continued)

*Primary Examiner* — Queenie S Dehghan
(74) *Attorney, Agent, or Firm* — Hayes Soloway P.C.

(57) ABSTRACT

A nitrous oxide gas mixer includes
at least one mixing chamber having at least one nitrous oxide gas connection and at least one oxygen gas connection for introduction of oxygen gas and nitrous oxide gas and at least one flow rate controller, by which a volume flow of the two gases can be respectively adjusted separately and/or together.
At least one $O_2$ emergency button is mounted to the mixing chamber for emergency flooding the mixing chamber with oxygen gas and/or with ambient air.

22 Claims, 4 Drawing Sheets

(51) Int. Cl.
  *A61K 33/00* (2006.01)
  *G06F 11/07* (2006.01)
  *G06F 3/0482* (2013.01)
  *G06F 3/16* (2006.01)
  *G06F 13/42* (2006.01)
  *B01F 15/00* (2006.01)
  *G06F 3/0488* (2013.01)
  *A61M 16/10* (2006.01)
  *A61M 16/12* (2006.01)
  *A61M 16/20* (2006.01)
  *A61M 16/00* (2006.01)
  *G01F 1/22* (2006.01)

(52) U.S. Cl.
  CPC .. *B01F 15/00162* (2013.01); *B01F 15/00175* (2013.01); *B01F 15/00305* (2013.01); *B01F 15/00311* (2013.01); *B01F 15/00402* (2013.01); *B01F 15/00422* (2013.01); *B01F 15/026* (2013.01); *B01F 15/0216* (2013.01); *G06F 3/0482* (2013.01); *G06F 3/0488* (2013.01); *G06F 3/167* (2013.01); *G06F 11/0745* (2013.01); *G06F 11/0769* (2013.01); *G06F 13/4282* (2013.01); *A61M 16/208* (2013.01); *A61M 2016/003* (2013.01); *A61M 2016/0027* (2013.01); *A61M 2202/0007* (2013.01); *A61M 2202/0208* (2013.01); *A61M 2202/0283* (2013.01); *A61M 2205/18* (2013.01); *A61M 2205/276* (2013.01); *A61M 2205/3334* (2013.01); *A61M 2205/3561* (2013.01); *A61M 2205/3584* (2013.01); *A61M 2205/3592* (2013.01); *A61M 2205/505* (2013.01); *A61M 2205/52* (2013.01); *A61M 2205/80* (2013.01); *A61M 2209/01* (2013.01); *B01F 2215/0032* (2013.01); *G01F 1/22* (2013.01)

(58) Field of Classification Search
  CPC ............ B01F 15/00422; B01F 15/0216; B01F 15/026; B01F 13/04; B01F 13/045
  See application file for complete search history.

(56) References Cited

U.S. PATENT DOCUMENTS

| | | | |
|---|---|---|---|
| 7,836,882 B1* | 11/2010 | Rumph | A61M 16/0051 128/203.12 |
| 2010/0132706 A1* | 6/2010 | Nashed | A61M 16/0078 128/203.28 |
| 2011/0100360 A1* | 5/2011 | Faram | A61H 9/0078 128/200.23 |
| 2012/0180789 A1* | 7/2012 | Tobia | A61M 16/0051 128/203.12 |
| 2012/0325208 A1* | 12/2012 | Heesch | A61M 16/104 128/203.25 |
| 2013/0206144 A1* | 8/2013 | Ahmad | A61M 16/00 128/204.23 |
| 2015/0075525 A1 | 3/2015 | Ahearn et al. | 128/203.14 |
| 2016/0228670 A1* | 8/2016 | Av-Gay | A61M 16/12 |

FOREIGN PATENT DOCUMENTS

| | | | |
|---|---|---|---|
| EP | 0100649 | 2/1984 | G05D 7/06 |
| EP | 1421966 | 5/2004 | A61M 16/00 |
| EP | 2702941 | 3/2014 | A61B 5/08 |
| GB | 1593219 | 7/1981 | A61M 17/00 |
| GB | 2176313 | 12/1986 | G05D 11/10 |
| WO | WO0003344 | 1/2000 | G06F 19/00 |
| WO | 2006/074251 | 7/2006 | |
| WO | WO2016005710 | 1/2016 | A61M 16/01 |

OTHER PUBLICATIONS

Extended European Search Report issued in application No. 16000433.9, dated May 9, 2016 (19 pgs).

Accutron Inc., Nitrous Oxide Conscious Sedation, Equipment and Accessories Catalog, 2011 (36 pgs).

European Communication issued in application No. 16 000 433.9, dated Feb. 27, 2018 (10 pgs).

\* cited by examiner

NITROUS OXIDE GAS MIXER FOR GENERATING A NITROUS OXIDE GAS MIX

BACKGROUND OF THE INVENTION

The nitrous oxide gas mixer presented here comprises at least one mixing chamber, within which an oxygen gas and a nitrous oxide gas are mixed together in respectively predeterminable volumes and/or mole contents to form the nitrous oxide gas mix.

The mixing chamber comprises at least one nitrous oxide connection and at least one oxygen gas connection, so that both the oxygen gas and the nitrous oxide gas are introduced into the mixing chamber via gas lines respectively connected to these connections.

Moreover, the nitrous oxide gas mixer comprises at least one concentration controller designed and provided for setting a mixing ratio between the oxygen gas introduced into the mixing chamber and/or the nitrous oxide gas introduced into the mixing chamber in a predeterminable manner.

Further, the nitrous oxide gas mixer described here comprises at least one flow rate controller, by means of which a volume flow of the two gases can in each case be adjusted separately and/or together.

However, such nitrous oxide gas mixers for generating a nitrous oxide gas mix are already known from the prior art.

What is in particular also known here are nitrous oxide gas mixers that comprise an $O_2$ emergency button. Such an $O_2$ emergency button allows pure oxygen to be introduced, in particular into the mixing chamber, for a patient in the case of an oversedation caused by the nitrous oxide gas or in the case of circulation problems. However, it is also conceivable, by actuating the $O_2$ emergency button, to reduce the nitrogen content to a specified percentage by volume, for example to 5 percent by volume in relation to the oxygen volume.

The reason is that the $O_2$ emergency button is one that preferably completely stops the supply of nitrogen and thus prevents any nitrogen inflow of the nitrous oxide gas into the mixing chamber. Insofar, a patient can be supplied with pure oxygen within the shortest period of time. It goes without saying that instead of pure oxygen, also any other nitrogen compounds, such as dinitrogen monoxide, may be used.

However, nitrous oxide gas mixers known from the prior art only have such $O_2$ emergency buttons that are provided hidden for example behind a concentration and/or a flow rate controller. Experience has shown that in the case of an oversedation, although an $O_2$ emergency button is present, the latter has often been overlooked, and for this reason valuable time passed until the user could find the $O_2$ emergency button.

SUMMARY OF THE INVENTION

On the basis of the above, it is therefore an object of the present invention to solve the above-mentioned problem and to provide a nitrous oxide gas mixer for generating a nitrous oxide gas mix, which allows in a particularly simple manner to carry out, in the case of an oversedation of a patient or in the case of circulatory problems of the patient, an emergency oxygen flooding of the mixing chamber of the nitrous oxide gas mixer.

In order to solve this problem and to avoid the above-mentioned problems, the present invention utilises, inter alia, the idea that for an emergency flooding of the mixing chamber with oxygen gas, at least one $O_2$ emergency button is mounted on the mixing chamber, which can be depressed in an actuation direction, wherein a preferably planar mounting surface of the $O_2$ emergency button, in respect of which the actuation direction extends perpendicularly in at least one point in the mounting surface, is free of further control elements.

This means, therefore, that there is no further control element in the whole vicinity in and along the plane of the mounting surface. Therefore, irrespective of the distance of a point in this plane and along the entire extension thereof relative to the $O_2$ emergency button, there is preferably no further control element provided. In particular, the mounting surface may also be free of mounting and/or fixing elements. For example, the $O_2$ emergency button is located centrally on the mounting surface.

This can mean that over the entire extension of the mounting surface, no mounting and/or fixing elements are provided thereon. Preferably, therefore, apart from the $O_2$ emergency button, no further element extends away from or into the mixing chamber along this mounting surface (which may for example be formed by an external surface of the mixing chamber). Also, this mounting surface may be free of screens or other analogue or digital representation units for representing e.g. pressure, temperature, flow rate.

Therefore, the mounting surface is for example that external surface of a mixing chamber housing, on which the $O_2$ emergency button is provided. However, the mounting surface may also be an external surface of a control unit of the nitrous oxide gas mixer, and such a control unit may then be provided remote from the actual mixing chamber housing.

In particular in the case of a planar mounting surface, this is a mounting surface that is free of gaps and interruptions. In particular, however, in the case of a planar mounting surface this can therefore be a surface that is either free of curves or has at least one curve. If the mounting surface is a surface that is free of curves, then this mounting surface constitutes a mounting plane. Therefore, the actuation direction is perpendicular at any point on such a mounting plane.

The term "control element" is used for such elements of a nitrous oxide gas mixer, which are suitable for adjusting a mixing ratio and/or for adjusting a flow rate of the gases. An on or off button of the nitrous oxide gas mixer is therefore different from such a control element. In other words, it is conceivable that apart from the $O_2$ emergency button, such an on and off button may additionally be provided on the mounting surface.

Insofar, it is therefore ensured in a particularly simple manner that the $O_2$ emergency button described here is not concealed from the user by any other control elements and is therefore optically pushed into the background, but is in particular provided in a central area of the mounting surface.

According to at least one embodiment, the nitrous oxide gas mixer comprises, for generating a nitrous oxide gas mixture, at least one mixing chamber, within which an oxygen gas and a nitrous oxide gas are mixed together in respectively predeterminable volumes and/or mole contents to form the nitrous oxide gas mix, wherein the mixing chamber has at least one nitrous oxide gas connection and at least one oxygen gas connection, so that both the oxygen gas and the nitrous oxide gas are introduced into the mixing chamber via gas lines respectively connected to these connections.

Moreover, the nitrous oxide gas mixer described here comprises at least one concentration controller designed and provided for adjusting a mixing ratio between the oxygen gas introduced into the mixing chamber and/or the nitrous oxide gas introduced into the mixing chamber in a predeterminable manner, wherein at least one flow rate controller, by means of which a volume flow of the two gases can in each case be adjusted separately and/or together, also forms part of the nitrous oxide gas mixer described here.

According to the invention, at least one $O_2$ emergency button is mounted on the mixing chamber for an emergency flooding of the mixing chamber with the oxygen gas and/or with ambient air, which $O_2$ emergency button can be depressed in an actuation direction, wherein a, preferably planar, mounting surface of the $O_2$ emergency button, in respect of which the actuation direction extends perpendicularly at least at one point in the mounting surface, is free of control elements.

In other words, for the first time a (in particular analogue) nitrous oxide gas mixer has been provided, wherein an alarm of an alarm unit notifies the user when a patient is supplied with insufficient oxygen and as a result, the user actuates the $O_2$ emergency button, or the latter is actuated fully automatically, in order to completely interrupt the supply of nitrous oxide gas to the patient, so that the latter is, in particular exclusively, supplied with oxygen. In order to assist in finding the emergency button especially quickly, the latter may be marked in red.

In particular, it is thus conceivable in this connection that, if the $O_2$ alarm sounds, this means that the mixer is supplied with insufficient $O_2$. In this case, nitrous oxide gas will preferably also cease to flow (100% nitrous oxide gas can even be lethal, nitrous oxide gas is blocked in the case of $O_2$ failure), and the empty $O_2$ bottle must be replaced or a plug-in connection to a gas ($O_2$) supply network has been disconnected or the supply network is empty.

It is thus conceivable that, if the alarm sounds, the $O_2$ flush button can no longer be pressed or no longer needs to be pressed.

In principle, however, the nitrous oxide gas mixer described here may also be used for a predeterminable mixing of other gases. For example, the nitrous oxide gas may then be replaced with another gas, in order to be then mixed with oxygen. However, it is also possible to replace the oxygen itself with another gas.

Moreover, it is conceivable that the nitrous oxide gas mixer described here is not only used within the context of dental treatment, but alternatively or in addition also within the context of another sedation process, for example before or during a birth phase in a delivery room. In this context it is conceivable that within the context of a gynaecological operation, the nitrous oxide gas mixer is provided with a mouth and nose mask via a demand valve.

However, it has in particular been shown that the nitrous oxide gas mixer described here may be provided with at least one input pressure reducer, by means of which a constant system pressure (individual gas pressures or the overall pressure in the mixing chamber) can be ensured.

According to at least one embodiment, the mixing chamber comprises a pre-chamber as well as a main chamber, wherein only the pre-chamber comprises the two gas connections and the main chamber is connected to the pre-chamber via at least one fluid connection, wherein an ambient air valve, instead of being fixed to a bracket for the main chamber, is located away from this bracket.

From the prior art, only such ambient air valves are known which are fixed on or above the main chamber, in particular to a bracket for the main chamber. If the main chamber is a gas bag, the ambient air valve is, in the prior art, frequently located on this bracket above the main chamber.

However, this often lead to an undesired introduction of blood, saliva etc. sucked in from the top through the ambient air valve. The impurities sucked in from the top via such an ambient air valve located above the gas bag often contaminate internal surfaces of the main chamber. Therefore, experience has shown that, whilst this is a space-saving positioning of the ambient air valve, however, when air is sucked in via the ambient air valve, dust, blood, saliva, detergent etc. can therefore enter into the main chamber via the ambient air valve.

It has therefore now been conceived to place this ambient air valve away from such a main chamber and in particular away from any such bracket for the main chamber. For example, such an ambient air valve is provided on a bracket that is different from the bracket for the main chamber. In particular, a surface normal of the valve opening of the ambient air valve may extend downwards and substantially parallel to the main extension direction of the main chamber. The ambient air valve may be a vacuum valve that automatically opens when the patient breathes in, if the main chamber has been breathed empty by the patient. As a result of placing the ambient air valve in such a way that its opening opens downwards in the direction of the bottom, no impurities will therefore be sucked in. Thus, the ambient air valve is protected from blood, saliva etc. The ambient air valve is in particular used for supplying the patient with ambient air once a gas reservoir (e.g. a gas bag) is empty.

According to at least one embodiment, at least the $O_2$ emergency button, preferably however also the concentration controller and the flow rate controller, are disposed on the pre-chamber. Insofar, the system of the mixing chamber is subdivided into a pre-chamber and a main chamber system. The pre-chamber is used for adjusting the composition of the nitrous oxide gas introduced into the main chamber in respect of the oxygen gas and nitrous oxide gas content, whereas the then finished nitrous oxide gas composition is introduced from the main chamber into a transfer hose. In this case, the transfer hose may then be connected to a corresponding nose mask.

According to at least one embodiment, the main chamber is formed by at least one gas bag. Insofar, instead of using a non-deformable component, the main chamber is then formed with such a component that is on the one hand not only deformable but is moreover also individually matched in its size to the correspondingly required amount of nitrous oxide gas.

According to at least one embodiment, the nitrous oxide gas mixer described here comprises at least one mixer control unit, wherein the mixer control unit comprises at least one digital control unit, wherein the control unit is designed in such a way that it controls the concentration controller and/or the flow rate controller on the basis of a user's specification. In particular, the mixer control unit can also control the concentration controller and/or the flow rate controller.

In other words, the mixer control unit described here and in particular the nitrous oxide gas mixer described here are, in terms of the application, controlled purely electronically. If, for example, the digital control unit and in particular a touchscreen of this digital control unit (and in this respect the control unit also comprises this touchscreen) are operated by the user, this control unit therefore controls the concentration controller and/or the flow rate controller purely electronically using at least one actuating unit.

As an alternative, the mixer control unit may also be one that comprises an analogue control unit. Such an analogue control unit is therefore free of a touchscreen and is controlled by the user for example manually, in particular exclusively manually. This mixer control unit therefore comprises the two controllers itself. To this end, the concentration controller and/or the flow rate controller comprise(s) operating elements, by means of which the user can manually control for example the concentration and the flow rate of the individual gases on the controllers.

In particular, however, such an analogue nitrous oxide gas mixer comprising the analogue control unit can comprise an audible warning means. Such a warning means, however, may also be located in the digital nitrous oxide gas mixer described above.

Should the flow of one or of both gases be interrupted, an in particular audible warning signal sounds immediately after the interruption of the respective gas flow.

Insofar, the nitrous oxide gas mixer described here is provided with such an audible alarm packet. For example, if the oxygen bottle runs out, an alarm may sound. Thus, if the oxygen supply is interrupted, no nitrogen will flow into the mixing chamber.

In particular, apart from a nitrogen supply interruption, also an interruption of the supply of nitrous oxide gas may be realised.

According to at least one embodiment, the digital control unit comprises at least one operating screen, in particular a touchscreen, by means of which, via a manual operation by the user, the concentration controller and/or the flow rate controller can be actuated electronically, preferably exclusively electronically.

According to at least one embodiment, the control unit is designed and provided to ensure that during operation, a navigation menu is displayed on the treatment screen, via which navigation menu treatment parameters, in particular volume and/or flow rate information with regard to the supplied oxygen and/or the nitrous oxide gas, are individually displayed.

According to at least one embodiment, the control unit is designed and provided to ensure that upon selection on the operating screen, the most recently treated patients are displayed, which is carried out either by means of an anonymised coding system or using the actual name or the corresponding patient ID.

One of the advantages of realising the control unit by means of the operating screen is that the user only needs to focus on the display of the operating screen in order to be able to control the nitrous oxide gas mixer in its entirety. In doing so, the operating screen may comprise real time displays of the nitrous oxide gas and/or the oxygen gas concentration within the nitrous oxide gas mix as well as individual flow rates in liters per minute or an overall flow rate of the gas mix. Such figure and volume data can therefore be adjusted by operating the operating screen in particular individually, i.e. via the operating screen itself.

According to at least one embodiment, the operating screen comprises at least one setting field, on which the user can manually set a change to the concentration of the oxygen gas and/or the nitrous oxide gas in predeterminable change increments, and this change to the concentration can preferably be adjusted just by operating the setting field. This offers the advantage that for example by means of a single depression of the setting field (=pushbutton), i.e. by means of pressing a single button, a change to the concentration for example of the oxygen gas, but alternatively or in addition also of the nitrous oxide gas may be adjusted. Therefore, the nitrous oxide gas mixer may by default be adjusted in such a way that the operating screen is set up so that the oxygen is added to a specified amount of nitrous oxide gas in 5 percent increments.

If the user presses this setting field (which is for example designated with "change of concentration: 1%/5%"), the nitrous oxide gas is increased or decreased in percent increments. A change can therefore be made at any time, e.g. if a child is to be sedated and the nitrous oxide gas has to be finely titrated.

However, apart from that it is also conceivable for the patient ID to be deposited or stored in the digital control unit. For example, prior to the sedation, an input field comprising letters and numbers opens on the operating screen, so that patient data can be entered accurately with a name or a patient number, which brings about significant advantages for the documentation of the treating person.

Moreover, the control unit can cause a menu item "call up last patient" to be displayed on the treatment screen. This may also be selected by the user, so that after selection on the operating screen, the most recently treated patient can be displayed. This can be carried out either by means of an anonymised coding system or via the actual name or the corresponding patient ID.

It is also possible to display the treatment time, the start of the sedation, the date and the maximum nitrous oxide gas value. Moreover, there is the possibility to delete the patient entry, and in this respect arrows located and appearing on the operating screen can be used for clicking onto the next patient.

Moreover, the operating screen described here can be used to carry out also further settings apart from changes to the concentration.

These further settings may comprise the time and the date. In this context, the time and the date may be adapted as required. Also, a volume of the alarm in the case of an interruption in the supply of one of the gases and of corresponding key tones may be set and controlled in a particularly simple manner. It is also possible to completely mute corresponding key tones.

Moreover, the operating screen described here offers the possibility of establishing a service culture for the nitrous oxide gas mixer. To this end it is possible to have the last and the next service date displayed. Moreover, it is possible to identify the hardware/software by the serial number of the device, which in turn can be displayed on the operating screen.

It is therefore possible to deliver the nitrous oxide gas mixer set up in such a way that by default a percentage is displayed on the operating screen as to how many percent by volume of nitrous oxide gas flow into the main chamber. If the user clicks on "show $O_2/N_2O$", the percentage of oxygen concentration will be displayed on the sedation display. A switch can be carried out at any time.

Moreover, the digital control unit described here may comprise an error memory that displays and stores a predetermined number of error messages, for example 20 error messages of the device.

There is in addition the possibility of deleting the memory. During service, it is in particular possible to have a predetermined number of errors, preferably all the errors, listed, in particular via a master SD card/dongle for service use. The errors can for example always be reviewed and exported in an administrator menu. In particular, the practitioner can moreover store protocols e.g. with a patient number on a USB stick and/or an SB port. Moreover, the practitioner can document the duration of treatment, the concentration etc.

According to at least one embodiment, the nitrous oxide gas mixer comprises at least one USB port and/or one SD card connection, so that for service use, a predefined number of errors, preferably all errors, can be handled, wherein in particular the errors can always be reviewed and exported in an administrator menu, and/or the practitioner can store protocols e.g. together with a patient number on a USB stick and/or an SB port, and/or the practitioner can document the treatment duration, the concentration etc.

Moreover, it is possible for the digital control unit described here to be internet enabled. For example, the digital control unit described here comprises an LAN or WLAN module, by means of which the digital control unit can be linked to another digital control unit and/or to a remotely located administrator via at least one standardised Internet protocol. For example, such an administrator can therefore externally log in to the digital control unit via the LAN or WLAN link, in order to be able to ensure remote support in this way. It is also possible, by means of such a control unit, for an administrator to carry out a boot or reboot or a remote diagnosis or remote settings on the digital control unit.

According to at least one embodiment, the nitrous oxide gas mixer comprises a remote control connection for a remote control, so that the control unit comprises a cable and/or IR and/or Bluetooth connection and/or can be operated wirelessly.

For example, the same functions can be operated via a smartphone or a tablet application by way of touchscreen inputs as can be via the display of the nitrous oxide gas mixer (increasing or decreasing the nitrous oxide gas concentration and the overall flow, initiate $O_2$ flush, discharge, show duration of treatment etc.).

Moreover, the nitrous oxide gas mixer described here may have, apart from the $O_2$ emergency button, a nitrous oxide gas cut-off, a limiting element for the nitrous oxide gas concentration and different connection sizes for nitrous oxide gas and oxygen.

According to at least one embodiment, at least one pressure sensor is provided on the mixing chamber, which pressure sensor measures at least one of the gas pressures, and the individual gas pressures can, during treatment or even prior to treatment, be set and/or read via a control unit integrated with the pressure sensor within a closed-loop control circuit. The gas pressures may in particular be those pressures that are predominant in supply bottles of the nitrous oxide gas mixer. For example, from the measurement of the respective one or more gas bottles a conclusion can be made as to the filling level of these gas bottles. This allows a conclusion to be made as to the remaining operating time in a particularly simple manner.

It would also be possible, on the basis of the knowledge of the bottle pressure, to draw a conclusion as to the possible remaining run-time on the basis of a reference to the amount of gas per minute that is administered at the time of treatment. (Message: e.g. "with constant respiratory minute volume/flow, there are still X minutes available" or "caution: gas supply will be finished in less than 30 minutes").

Moreover, apart from the pressure sensor, it is also possible, in particular by integrating at least one of the flow meters in the closed-loop control circuit, to calculate in advance by means of a computing unit how long the discharge of a corresponding gas from the respective gas bottle can be maintained under a specifiable pressure.

According to at least one embodiment, the nitrous oxide gas mixer moreover comprises, apart from the $O_2$ emergency button, a nitrous oxide gas discharge button, via which the nitrous oxide gas can be immediately charged for example from the mixing chamber, over the duration of a period of time that can be individually set by a user and/or, via the nitrous oxide gas discharge button, a supply of nitrous oxide gas into the mixing chamber can be immediately interrupted for the duration of this period of time, so that only oxygen is supplied to the mixing chamber. To this end, the nitrous oxide gas discharge button can be in operative mechanical and/or electrical connection with an exhaust valve of the mixing chamber, via which the nitrous oxide gas can be exhausted from the mixing chamber.

In this connection, the following operation scenario would be conceivable:

The nitrous oxide gas discharge button can be used to immediately discharge the sedation agent (nitrous oxide gas) from the mixing chamber; in this case a countdown will run. During this time, only 100% of $O_2$ will flow, nitrous oxide gas will not flow any longer. After e.g. 5 minutes of pure oxygen, the effect of the nitrous oxide gas will have died down, because nitrous oxide gas is not metabolised and can be quickly exhaled. The user can individually set the discharge time.

Instead of providing a separate button for the above-mentioned purposes, the function of the immediate discharge or interruption of the supply of the nitrous oxide gas as described above can also be carried out via the $O_2$ emergency button described above. In this respect it is conceivable that upon pressing the $O_2$ emergency button in a first setting, preferably exclusively oxygen is fed into the mixing chamber, and in a second position, the $O_2$ emergency button in addition or instead has the function of discharging any residual nitrous oxide gas still remaining therein from the mixing chamber. Therefore, in the second position, the mixing chamber is exhausted.

According to at least one embodiment, the nitrous oxide gas discharge button comprises a timer element and is controlled by such a timer element, so that upon expiration of a period of time set on the timer element, the nitrous oxide gas discharge button will automatically return into a zero position. The zero position is therefore the setting of the nitrous oxide gas discharge button, in which the latter is moved into an off position.

According to at least one embodiment, at least one flow rate sensor for measuring a flow rate and/or a volume flow of the gas respectively carried in the gas lines and/or for measuring a vacuum throughflow of suction is provided on or in at least one of the gas lines and/or directly on the mixing chamber. For example, these functions could be carried out by a common and/or by respectively different sensors, depending on the separation of tasks.

As the gas flow passes the sensor, heat from the sensor is carried to a medium, for example in the medium. As the flow increases, also the volume of heat that is transferred increases. If the heat transfer is known, then the rate of flow can be determined using the amount of tension equalisation necessary for maintaining a constant temperature difference.

In particular, the entire device may be free of measurement propellers for measuring a gas volume flow. Instead, the flow rate sensor described above may be exclusively used for measuring the gas volume flow. Unlike the "propellers", the sensor operates substantially independently of pressure and for example even of temperature. Also, the response time is shorter because the mass inertia of the propellers results in a delay in starting and stopping.

According to at least one embodiment, this flow rate sensor determines the flow rate and/or the volume flow of the respective gas, preferably exclusively on the basis of a heat transport measurement of the gas.

Moreover, suction control immediately above the mixing chamber can be carried out as follows:

The mixture of nitrous oxide gas and oxygen must be sucked off for protecting personnel (the specification is for example a vacuum suction output of 45 l/min).

An additional flow sensor for measuring the vacuum flow of the suction may be integrated in the digital mixer. A further measurement chamber is present in the mixer, and this is a thermo or ultrasound measurement method.

The software processes the input of the flow sensor and the touchscreen display indicates how strong the current throughflow or the current suction output is. It is also supposed to be possible to call up on the touchscreen a display of how many l/m in are sucked off in real time. Moreover, it is supposed to be possible that the suction output can be modified via the touchscreen setting.

A minimisation of the suction output is carried out by way of reducing the lumen of a control valve or a magnetic valve, an increase of the suction output can be achieved by increasing the lumen.

The display shows whether the flow is all right (e.g. at 45 l/min in it is highlighted in green). If the throughflow is too strong or too weak, it is highlighted in red. The software automatically detects if the throughflow is too low. In this case it will cause the control valve to be opened, and if the throughflow is still too low, the control valve can also be completely opened, so that the throughflow through the control valve is not minimised at all. If the throughflow is too strong, then this will be detected by the software and the control valve will be slightly closed, so that 45 l/min are achieved. Moreover, it is also possible to close the control valve completely via the touchscreen display, in order to stop the flow.

The vacuum control valve will not open until nitrous oxide gas flows, which contaminates ambient air, which means that only then suction will take place. Thus, a patient can breathe pure oxygen without resistance by the suction, because the suction will then be closed. The control valve will close again after the nitrous oxide gas is switched off, with a delay of e.g. 30 seconds, which means suction is closed. The delay of approx. 30 seconds is important because there will still be nitrous oxide gas in the patient's lungs, which has to be exhaled first.

According to at least one embodiment, the nitrous oxide gas mixer comprises gas valves for controlling and/or passing through the oxygen and the nitrous oxide gas, which gas valves use in each case a control piston instead of rubber membranes as the control means.

Insofar, the nitrous oxide gas mixer described above may be free of membranes, in particular of rubber membranes. Rubber membranes are often used within the context of a valve control due to their low material costs. However, it has been recognised that after prolonged periods of use and/or under great pressure differentials, such rubber membranes often become cracked and may even, after a short period of time, become leaky. Instead of the use of rubber membranes, it has now been conceived to use corresponding valve pistons. In this context, the valve pistons have the same switching functions as the rubber membranes described above. The reason for this is, inter alia, that the pistons are guided within piston housings and the pistons may here adopt substantially two switching conditions. In a first switching condition, a fluid connection between a valve inlet and a valve outlet is at least partially free for the gas fluid, and in a second switching condition, the piston at least partially blocks a passage for the fluid between the valve inlet and the valve outlet.

According to at least one embodiment, the nitrous oxide gas mixer described here does not have an on/off button. Insofar it can be avoided that a user, for example in an emergency, is not absolutely clear about the fact that the nitrous oxide gas mixer has to be switched off using such an on/off button. The nitrous oxide gas mixer described here can therefore be free of such an on/off button and can therefore, during use, simply be connected and disconnected by plugging into and out of a mains outlet.

However, alternatively the nitrous oxide gas mixer can still include an on/off button if the on/off button is designed in such a way that it has to be pressed continuously for a predetermined period of time, for example at least two seconds, so that the treating person will not unintentionally switch the device off if they want to actuate the $O_2$ emergency button. Advantageously, the on/off switch is not located on the touchscreen.

Moreover, an overall flow can be increased, in particular by means of the nitrous oxide gas mixer described here. For example, the nitrous oxide gas mixer described here allows an overall flow of 20 l/min or higher, so that the main chamber, i.e. for example the breathing bag, will always be sufficiently filled with nitrous oxide gas and sedation is effective.

The reason is that, if such an overall flow is selected to be too low, for example in a region of just 8-10 l/min, a patient will often breathe the main chamber empty, because an anxious patient breathes more quickly and more l/min, so that the ambient air valve will open, so that ambient air is sucked in and sedation can therefore no longer be effective. In particular, it has been shown that a volume of the main chamber in a region of <10 l often is selected to be too low because an anxious patient will breathe with a very high frequency.

As has already been mentioned above, also the readability of the nitrous oxide gas concentration is significantly improved compared to the prior art. Compared to already known nitrous oxide gas mixers, it is here, inter alia, proposed to display a percentage nitrous oxide gas concentration of the overall amount of gas breathed in by the patient instead of merely indicating a percentage oxygen gas concentration. Thus, the practitioner no longer needs to convert the figures, so that an incorrect setting will be avoided.

For safety reasons, the nitrous oxide gas concentration scale as proposed here starts at 0% nitrous oxide gas and ends with 50% or 60% or 70% of nitrous oxide gas (depending on the variant). Also an overall flow stop and/or a separate nitrous oxide gas concentration control stop may be provided on the nitrous oxide gas mixer, which minimises risks in connection with the control of the gas flow. The reason is that by means of such a stop it is avoided that too much gas flows. In particular, the overall flow stop can prevent that more than e.g. 20 liters per minute of mixed gas from flow.

According to at least one embodiment, the nitrous oxide gas mixer comprises a voice control device that is designed and provided to control preferably all of the functions via an acoustic detection of the voice of a practitioner. A voice signal that is detected by the voice control device may for example relate to various voice commands such as "total flow 10 l/min", "close suction", etc.

BRIEF DESCRIPTION OF THE DRAWINGS

The nitrous oxide gas mixer described here will be described in more detail below by means of embodiment examples and the associated figures.

In the figures, same or components or components with the same effect were each provided with the same reference numerals. The elements shown here are not to be regarded as true to scale, rather individual elements may be shown exaggerated in order to enhance understanding.

DETAILED DESCRIPTION OF THE INVENTION

Figure 1A:
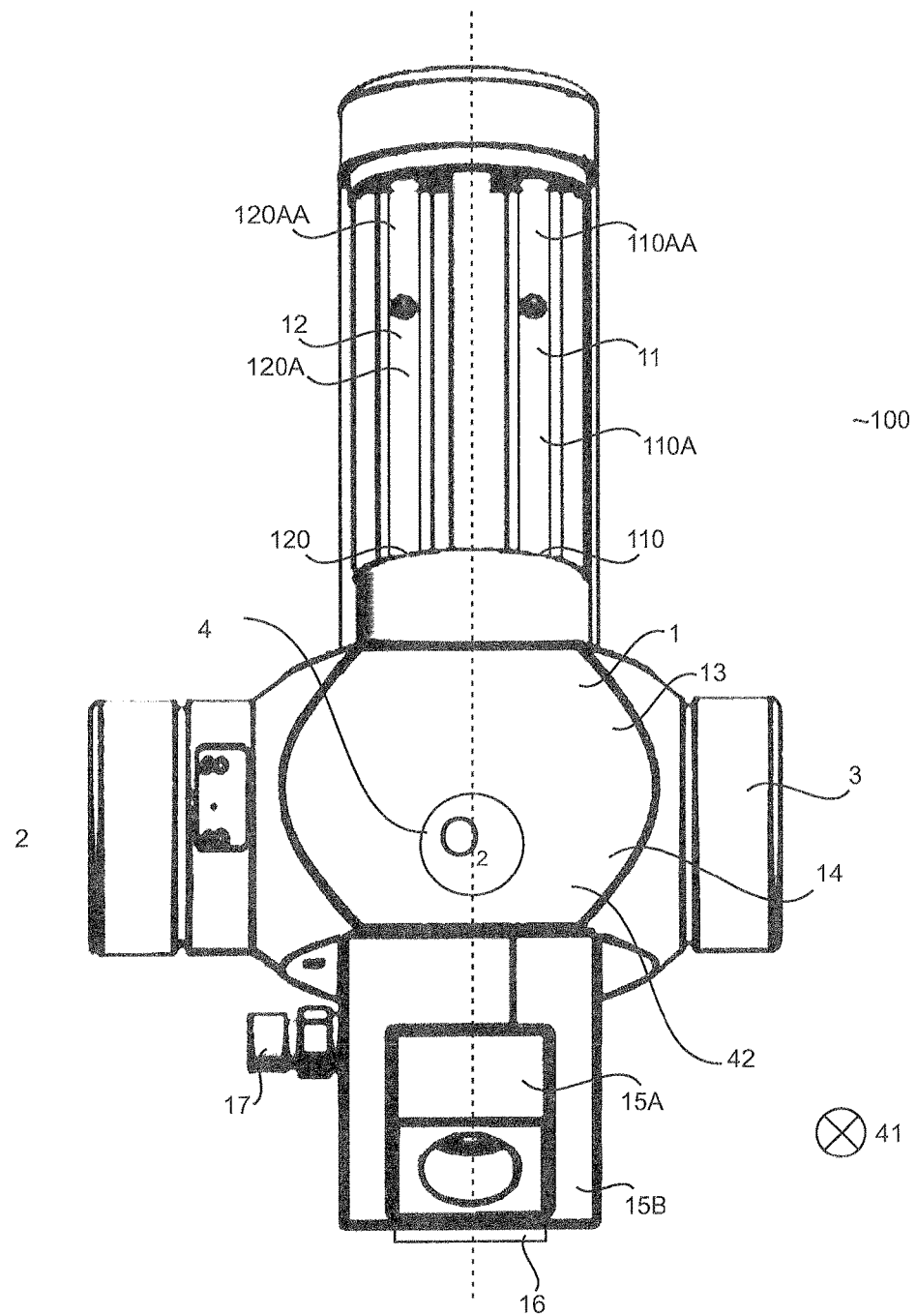
FIGS. 1A, 1B, 1C show a schematic lateral view of an embodiment example of an analogue nitrous oxide gas mixer described here.

FIG. 1A shows an embodiment example of an analogue nitrous oxide gas mixer 100 described here.

In this figure it can be particularly easily seen that the nitrous oxide gas mixer 100 described here comprises, for generating a nitrous oxide gas mix, at least one mixing chamber 1, within which an oxygen gas 11 and a nitrous oxide gas 12 are mixed together in respectively predeterminable volumes and/or mole contents to form the nitrous oxide gas mix 13, wherein the mixing chamber 1 has a nitrous oxide gas connection 120 (see FIG. 10) and an oxygen gas connection 110 (see FIG. 1C), so that both the oxygen gas and the nitrous oxide gas are introduced into the mixing chamber via corresponding gas lines 110A, 120A mounted to these connections. Insofar, FIG. 10 shows a perspective rear view of the front view shown in FIG. 1A of the nitrous oxide gas mixer.

In particular, the gas lines 110A (oxygen), 120A (nitrogen) are designed in such a way that they comprise respective flow meters 110AA and 120AA, by means of which the respective flow rate of the gases over a pressure-displaceable flow ball can be read off from the respective measurement scales.

Moreover, a concentration controller 2 can be seen from FIG. 1, by means of which a mixing ratio between the oxygen gas 11 introduced into the mixing chamber 1 and/or the nitrous oxide gas 12 introduced into the mixing chamber 1 can be set in a predeterminable manner, and also a flow rate controller 3 can be seen, by means of which a volume flow of the two gases 11, 12 can be adjusted separately and/or together.

What can be seen particularly well in FIG. 1 is the $O_2$ emergency button 4 according to the invention, which is always present and which is used for emergency flooding of the mixing chamber 1 with the oxygen gas 11 and/or with ambient air.

If the $O_2$ emergency button 4 is pressed, exclusively the oxygen gas 11 will get into the mixing chamber 1. Any supply of the nitrous oxide gas 12 is therefore completely prevented. To this end, the $O_2$ emergency button 4 is located on a mixing chamber housing 1A of the mixing chamber 1 and can be depressed in an actuation direction 41, and the mixing chamber housing of the mixing chamber 1 comprises a mounting plane 42.

Therefore, the $O_2$ emergency button 4 is operatively connected with the mixing chamber 1 at this mounting surface 42 and can also be depressed in the direction of the mounting surface 42 in the actuation direction 41.

It is now important to note that the mounting surface 42 is free of any further control elements. This means in particular that the concentration controller 2 and the flow rate controller 3 are not located on the mounting surface 42 of the mixing chamber housing of the mixing chamber 1, but are located on sides of the mixing chamber housing 1A of the mixing chamber 1 that are different therefrom. This has the direct consequence that the side on which the $O_2$ emergency button 4 is located and the sides on which the concentration controller 2 and/or the flow rate controller 3 are located on the mixing chamber housing 1A of the mixing chamber 1 are different from each other. Insofar it is ensured that a user can, in an emergency, immediately find the $O_2$ emergency button 4 and that the latter is neither concealed by the concentration controller 2 nor by the flow rate controller 3 or any other control elements.

Figure 1B:
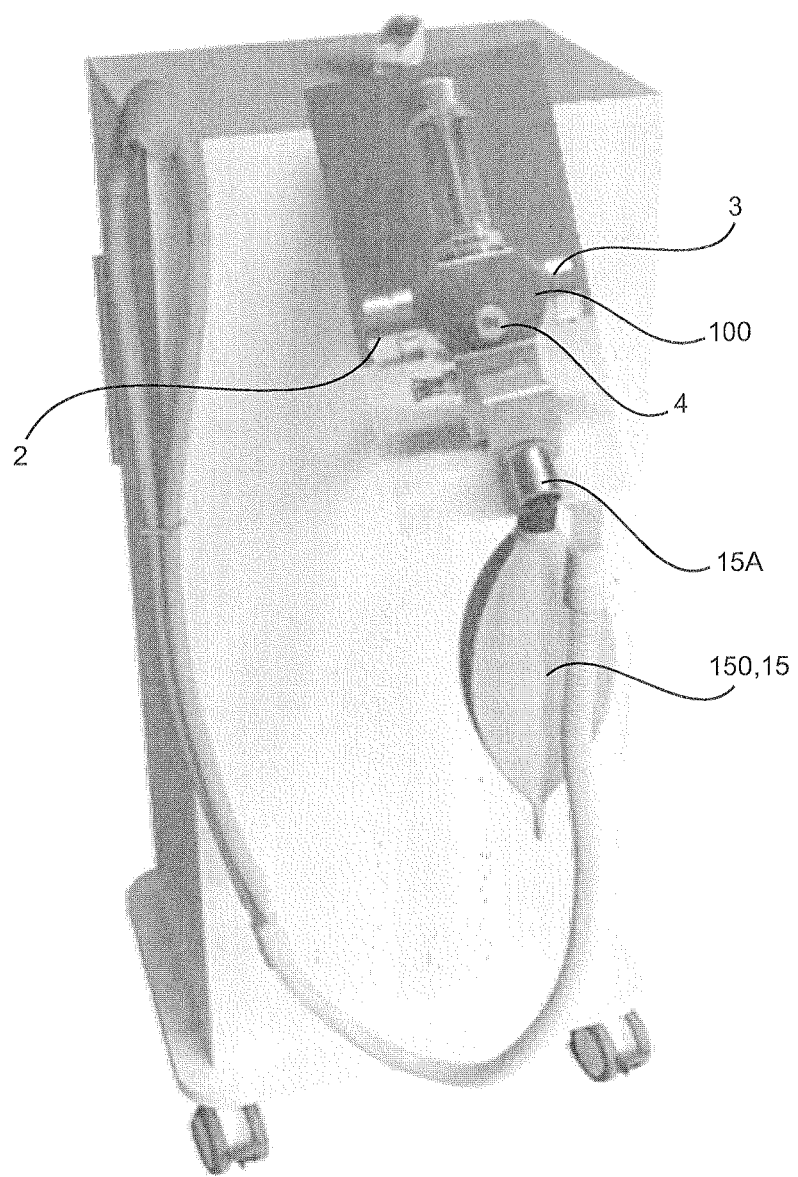
Figure 1C:
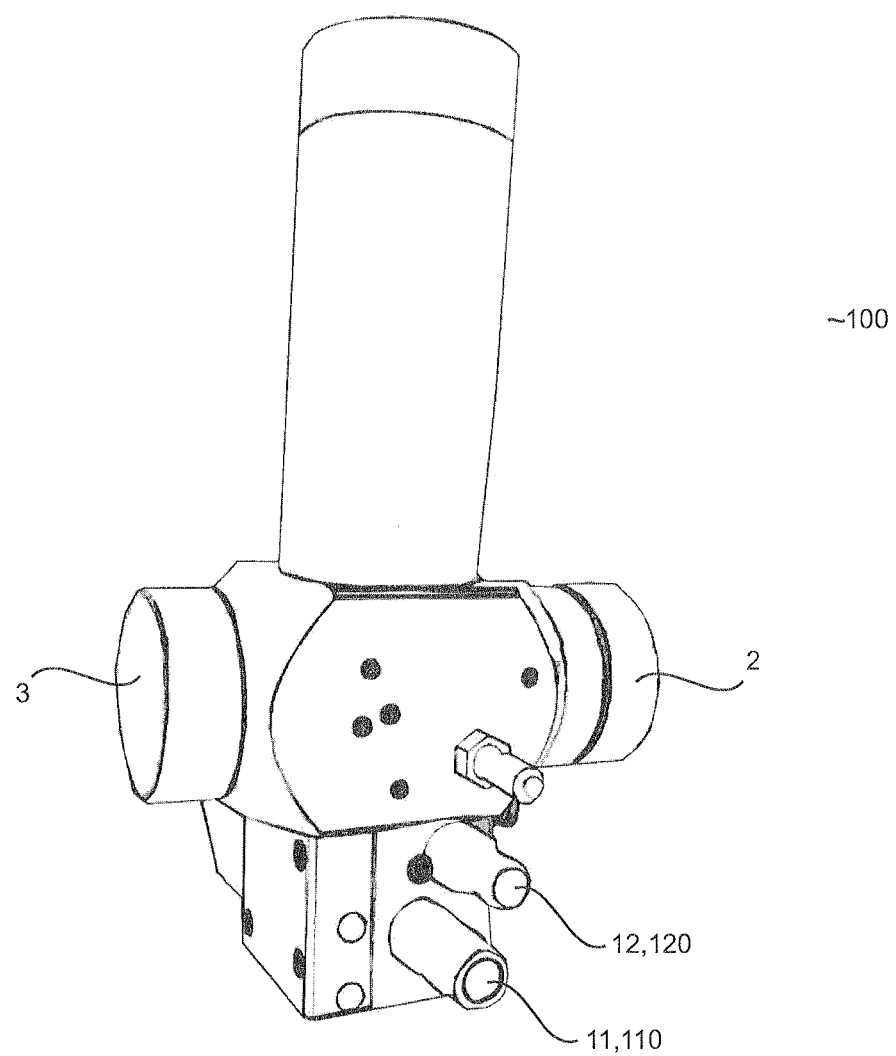

In FIG. 1B, the nitrous oxide gas mixer 100 described in FIG. 1A can be seen in a perspective view, and compared to FIG. 1A, it can now be better seen that the mixing chamber 1 is formed with a pre-chamber 14 as well as a main chamber 15. The main chamber 15 forms a gas bag 150. The gas bag 150, i.e. the main chamber 15, is connected with the pre-chamber 14 via a fluid connection.

Also an ambient air valve 16 can be seen, which is located, instead of being mounted on the bracket 15A (bag T) for the main chamber 15, away from the main chamber 15 so as to prevent any saliva, blood etc. from getting into the bag T (e.g. spray water etc.) through the patient during their treatment, but in particular also when breathing in. In particular, it can be seen from FIG. 1B that the ambient air valve 16 is provided on a further bracket 15B and can, in the direction of the main chamber 15, for example also in the direction of a longitudinal axis L of the nitrous oxide gas mixer 100, be closed and opened. If the patient breathes the main chamber 15 empty, the ambient air valve 16 will, whilst the patient breathes in after in particular completely emptying the main chamber 15, automatically open, so that a fluid line running between a nose mask connection 17 of the nitrous oxide gas mixer 1 and the main chamber 15 is filled with ambient air. The patient will therefore always be supplied with sufficient oxygen.

Figure 2A:
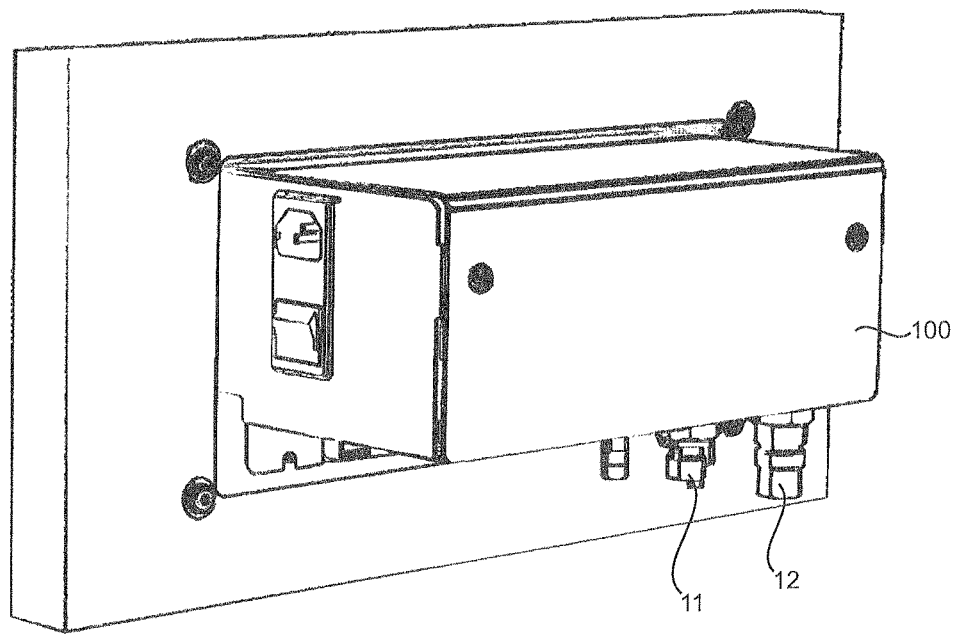
FIGS. 2a and 2b show schematic perspective views of an embodiment example of a digital nitrous oxide gas mixer described here.
Figure 2B:
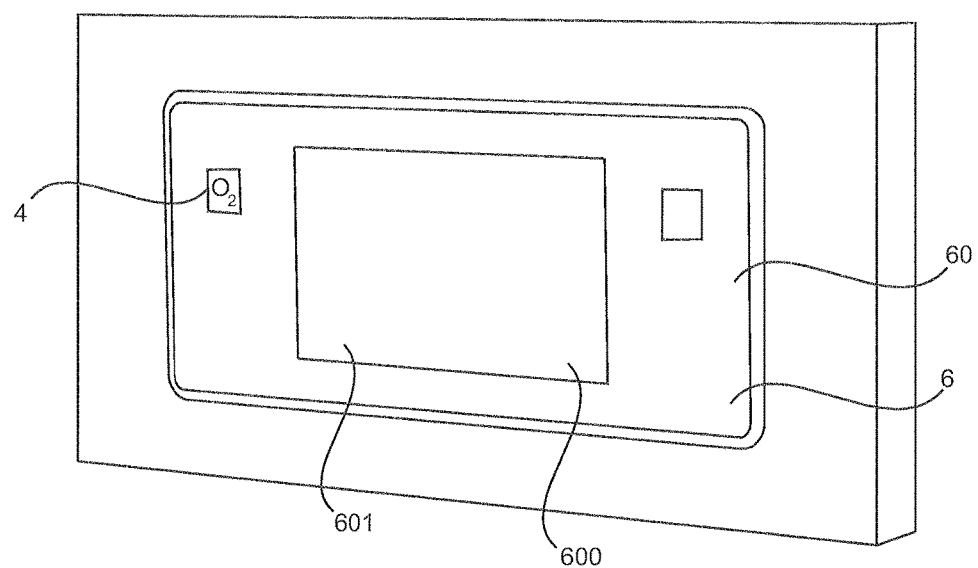

FIGS. 2A and 2B show a schematic perspective view of an embodiment example of a digital nitrous oxide gas mixer 100 described here.

As can be seen from the perspective rear view according to FIG. 2A, the nitrous oxide gas mixer 100 shown for example in FIGS. 1A, 1B is accommodated in a housing, in which the various connections protrude from the housing so as to be connected to the corresponding gas lines.

FIG. 2B shows a front view in which a mixing control unit 6 is represented that comprises a digital control unit 60. In this connection, the digital control unit 16 is designed in such away that it can control the concentration controller 2 and/or the flow rate controller 3 via a user specification by pressing the buttons of an operating screen 600. For the digital control unit 60 described here comprises an operating screen 600, by means of which the concentration controller and/or the flow rate controller can be electronically, preferably exclusively electronically, open- and/or closed-loop controlled. In such a case, the operating screen 600 can therefore be located on a further mounting surface, and this further mounting surface may be different from the mounting surface 42. Moreover, the operating screen 600 does here not fall under a control element located on the mounting surface. This may mean that in the example of FIG. 2B, the mounting surface is a surface that excludes the operating screen 600 and then at least partially encircles it. This may mean that this actuator unit can then actuate the concentration controller and the flow rate controller, for example mechanically, via electronic signals transmitted from the operating screen to an actuating unit.

In particular, the operating screen 600 comprises at least one setting field 601, on which the user can manually set a change to the concentration of the oxygen gas 11 and/or of the nitrous oxide gas 12 in predeterminable change increments, and the change to the concentration can in the present embodiment example be set only by way of operating the setting field 601. However, in any case the $O_2$ emergency button 4 can again be seen which, apart from a on/off button, is the only button within the mounting surface 42 of the operating screen 600, so that on the digital nitrous oxide gas mixer 100, too, it is ensured according to the invention that in an emergency, the treating physician can particularly rapidly flood the patient with oxygen.

The invention is not limited to the embodiment examples, rather the invention comprises any new feature as well as any combination of features, which in particular also includes any combination of the patent claims, even if this feature or this combination itself is not explicitly indicated in the patent claims or in the embodiment examples.

LIST OF REFERENCE NUMERALS

1 Mixing chamber
1A Mixing chamber housing
2 Concentration controller
3 Flow rate controller/flow controller
4 $O_2$ emergency button
6 Mixer control unit
11 Oxygen gas
12 Nitrous oxide gas
13 Nitrous oxide gas mix
14 Pre-chamber
15 Main chamber
15A Bracket
15B Further bracket
16 Ambient air valve
41 Actuation direction
42 Mounting surface
60 Control unit
100 Nitrous oxide gas mixer
110 Oxygen gas connection
110A, 120A Gas lines for the two gases to be mixed
110AA, 120AA Flow meter
120 Nitrous oxide gas connection
150 Gas bag
600 Operating screen
601 Setting field

The invention claimed is:

1. A nitrous oxide gas mixer for generating a nitrous oxide gas mix, comprising:
    at least one mixing chamber, within which an oxygen gas and a nitrous oxide gas are mixed together in respectively predeterminable volumes and/or mole contents to form the nitrous oxide gas mix, wherein
    the mixing chamber has at least one nitrous oxide gas connection and at least one oxygen gas connection, so that both the oxygen gas and the nitrous oxide gas may be introduced into the mixing chamber via on/off buttons and gas lines respectively mounted to these connections,
    at least one concentration controller, adapted for setting a mixing ratio between the oxygen gas introduced into the mixing chamber and/or the nitrous oxide gas introduced into the mixing chamber in the nitrous oxide gas mix in a predeterminable manner,
    at least one flow rate controller by which a volume flow of the individual oxygen and nitrous oxide gases or the mixed oxygen and nitrous oxide gas can be adjusted,
wherein
    at least one $O_2$ emergency button operatively connected to the mixing chamber for emergency flooding the mixing chamber with the oxygen gas and/or with ambient air, wherein the on/off button of the nitrous oxide gas mixer is different from the concentration controller element, and the $O_2$ emergency button can be depressed in an actuation direction, wherein a planar mounting surface of the $O_2$ emergency button, in respect of which the actuation direction extends perpendicularly at least at a point in the mounting surface, is tree from other control elements, selected from a group comprising elements adapted for adjusting a mixing ratio and/or for adjusting a flow rate of the gases, screens or other analogue or digital representation units, and is also free of mounting and/or fixing elements, and therefore there is no other control element or mountings and/or fixing element located in the entire vicinity along and in the plane of the mounting surface, and wherein
    the mounting surface is an external surface of a mixing chamber housing, on which the $O_2$ emergency button is located, or
    the mounting surface is an external surface of a control unit of the nitrous oxide gas mixer, located remote from the mixing chamber housing.

2. The nitrous oxide gas mixer as claimed in claim 1, wherein
    the mixing chamber comprises a pre-chamber as well as a main chamber, wherein only the pre-chamber comprises the two gas connections and the main chamber is connected to the pre-chamber via at least one fluid connection, wherein an ambient air valve is located remote from the pre-chamber.

3. The nitrous oxide gas mixer as claimed in claim 2, further comprising at least the $O_2$ emergency button provided on the pre-chamber.

4. The nitrous oxide gas mixer as claimed in claim 3, further comprising at least one mixer control unit, wherein the mixer control unit comprises at least one digital control unit, wherein the control unit is designed such that it controls said concentration controller and/or said flow rate controller on the basis of the user's specification.

5. The nitrous oxide gas mixer as claimed in claim 2, further comprising at least one mixer control unit, wherein the mixer control unit comprises at least one digital control unit, wherein the control unit is designed such that it controls said concentration controller and/or said flow rate controller on the basis of the user's specification.

6. The nitrous oxide gas mixer as claimed in claim 2, wherein the ambient air valve has a valve opening which extends downwards and substantially parallel to the planar mounting surface of the main chamber.

7. The nitrous oxide gas mixer as claimed in claim 2, wherein
    the mixer comprises at least one USB port and/or one SD card connection, so that for service use, a predetermined number of errors, preferably all errors, can be handled, in particular wherein
    the errors can always be read and exported in an administrator menu, and/or the practitioner can store protocols e.g. together with a patient number on a USB stick and/or an SB port, and/or the practitioner can document the duration of treatment, the concentration etc.

8. The nitrous oxide gas mixer as claimed in claim 2, further comprising at least one pressure sensor provided on the mixing chamber, which pressure sensor measures at least one of the gas pressures, wherein the individual gas pressures can be read and/or set during or prior to the treatment via a control unit integrated within a closed-loop control circuit.

9. The nitrous oxide gas mixer as claimed in claim 2, wherein said mixer comprises a voice control device, which is designed and provided to control operating functions of the mixer via an acoustic detection of a voice of a practitioner.

10. The nitrous oxide gas mixer as claimed in claim 1, further comprising a digital control unit comprising at least one operating screen, in particular a touchscreen, by-which the concentration controller and/or the flow rate controller can be electronically operated via a manual operation by the user, wherein the operating screen comprises at least one setting field, on which the user can manually set a change to the concentration of the oxygen gas and/or of the nitrous oxide gas in predeterminable change increments, and wherein the change to the concentration can be set by actuating said setting field.

11. The nitrous oxide gas mixer as claimed in claim 10, wherein the control unit is designed and provided to indicate during operation a navigation menu on a treatment screen, which navigation menu can be used to individually indicate and/or store volume and/or flow rate information with regard to the oxygen and/or nitrous oxide gas supplied.

12. The nitrous oxide gas mixer as claimed in claim 1, wherein the nitrous oxide gas mixer further comprises, apart from the $O_2$ emergency button, a nitrous oxide gas discharge button, via which the nitrous oxide gas can be immediately discharged from the mixing chamber over a duration of a period of time that can be individually set by a user, and/or a supply of nitrous oxide gas into the mixing chamber can be immediately interrupted for the duration of the period of time, so that only oxygen is fed into the mixing chamber.

13. The nitrous oxide gas mixer as claimed in claim 1, wherein the nitrous oxide gas discharge button comprises a timer element or is controlled by a timer element, so that upon expiration of a period of time set on the timer element, the nitrous oxide gas discharge button automatically returns to an off position.

14. The nitrous oxide gas mixer as claimed in claim 1, further comprising at least one flow rate sensor for measuring a flow rate and/or a volume flow of the gas respectively introduced into the gas lines and/or for measuring a vacuum throughflow of a suction is provided on or in at least one of the gas lines and/or directly on the mixing chamber.

15. The nitrous oxide gas mixer as claimed in claim 14, wherein the flow rate sensor determines the flow rate and/or the volume flow of the respective gas, on a basis of temperature measurements of the gas.

16. The nitrous oxide gas mixer as claimed in claim 1, further comprising a control unit designed and provided for displaying, once selected, an identification of a patient being treated on the operating screen, which is carried out using an anonymised coding system or using the actual name or the corresponding patient ID.

17. The nitrous oxide gas mixer as claimed in claim 1, wherein said mixer comprises gas valves for controlling and/or passing through the gas flow of the oxygen and/or of the nitrous oxide gas, which gas valves each provide a control piston instead of rubber membranes as the control device.

18. The nitrous oxide gas mixer as claimed in claim 1, wherein the mixer comprises an audible warning device, wherein such a warning device is designed and provided for interrupting the flow of one or both gases, wherein in particular an audible warning signal will sound immediately after the interruption of the respective gas flow.

19. The nitrous oxide gas mixer as claimed in claim 1, wherein said mixer comprises a remote control connection for a remote control, wherein the control unit comprises a cable and/or IR and/or Bluetooth connection and/or can be operated wirelessly.

20. The nitrous oxide gas mixer as claimed in claim 1, wherein the nitrous oxide gas mixer does not have an on/off button.

21. A nitrous oxide gas mixer as claimed in claim 1, wherein the $O_2$ emergency button is provided in a central area of the mounting surface.

22. A nitrous oxide gas mixer for generating a nitrous oxide gas mix, comprising:

at least one mixing chamber, within which an oxygen gas and a nitrous oxide gas are mixed together in respectively predeterminable volumes and/or mole contents to form the nitrous oxide gas mix, wherein the mixing chamber has at least one nitrous oxide gas connection and at least one oxygen gas connection, so that both the oxygen gas and the nitrous oxide gas are introduced into the mixings chamber via on/off buttons and gas lines respectively mounted to these connections, at least one concentration controller, adapted for setting a mixing ratio between the oxygen gas introduced into the mixing chamber and/or the nitrous oxide gas introduced into the mixing chamber in the nitrous oxide gas mix in a predeterminable manner, at least one flow rate controller by which a volume flow of the individual gases or the mixed gases can be adjusted, wherein at least one $O_2$ emergency button is operatively connected to the mixing chamber for emergency flooding the mixing chamber with the oxygen gas and/or with ambient air, wherein the on/off button of the nitrous oxide gas mixer is different from a control element, and the $O_2$ emergency button can be depressed in an actuation direction, wherein a planar mounting surface of the $O_2$ emergency button, in respect of which the actuation direction extends perpendicularly at least at a point in the mounting surface, is free from other control elements or gaps and interruptions, and therefore there is no other control element or gaps and interruptions located in the entire vicinity along and in the plane of the mounting surface, and wherein the mounting surface is an external surface of a mixing chamber housing, on which the $O_2$ emergency button is located, or the mounting surface is an external surface of a control unit of the nitrous oxide gas mixer, wherein such control unit is located remote from the mixing chamber housing.

\* \* \* \* \*